United States Patent
Barral et al.

(10) Patent No.: US 10,600,183 B2
(45) Date of Patent: Mar. 24, 2020

(54) DETECTION OF BLOOD VESSELS

(71) Applicant: Verily Life Sciences LLC, Mountain View, CA (US)

(72) Inventors: Joëlle K. Barral, Mountain View, CA (US); Mikhail Erofeev, Moscow (RU)

(73) Assignee: Verily Life Sciences LLC, South San Francisco, CA (US)

(*) Notice: Subject to any disclaimer, the term of this patent is extended or adjusted under 35 U.S.C. 154(b) by 110 days.

(21) Appl. No.: 15/923,399

(22) Filed: Mar. 16, 2018

(65) Prior Publication Data

US 2018/0276823 A1    Sep. 27, 2018

Related U.S. Application Data

(60) Provisional application No. 62/474,774, filed on Mar. 22, 2017.

(51) Int. Cl.
*G06T 7/00* (2017.01)
*A61B 5/024* (2006.01)
(Continued)

(52) U.S. Cl.
CPC ........ *G06T 7/0016* (2013.01); *A61B 1/00009* (2013.01); *A61B 1/00016* (2013.01); *A61B 1/00149* (2013.01); *A61B 5/024* (2013.01); *A61B 5/7207* (2013.01); *A61B 5/7425* (2013.01); *A61B 90/37* (2016.02); *G06T 7/215* (2017.01); *A61B 1/00045* (2013.01); *A61B 1/07* (2013.01); *A61B 17/3211* (2013.01);
(Continued)

(58) Field of Classification Search
CPC ............ A61B 1/00016; A61B 1/00149; A61B 1/00009; A61B 5/024; A61B 5/7207; A61B 5/7425; A61B 90/37; G06T 7/0016
See application file for complete search history.

(56) References Cited

U.S. PATENT DOCUMENTS

| 5,331,550 A | 7/1994 | Stafford et al. |
|---|---|---|
| 7,558,320 B2 | 7/2009 | Winder et al. |

(Continued)

OTHER PUBLICATIONS

"Video Magnification in Presence of Large Motions," Mohamed A. Elgharib et al., Qatar Computing Research Institute, MIT CSAIL, 9 pages.

(Continued)

*Primary Examiner* — Leon Flores
(74) *Attorney, Agent, or Firm* — Christensen O'Connor Johnson Kindness PLLC (57) ABSTRACT

A system for the detection of blood vessels includes an image sensor coupled to generate video data including a sequence of images of the blood vessels, and a heart rate monitor to measure a heart rate of a patient and to generate heart rate data. A controller is coupled to the image sensor to receive the video data, and coupled to the heart rate monitor to receive the heart rate data. The controller includes logic that when executed by the controller causes the controller to perform operations including isolate localized motion of the blood vessels in the video data using the heart rate data. The controller also computes a blood vessel mask (that includes differences between the video data and the localized motion of the blood vessels) and combined video data (that includes the video data and the blood vessel mask).

21 Claims, 4 Drawing Sheets

(51) Int. Cl.
  *A61B 1/00*   (2006.01)
  *A61B 5/00*   (2006.01)
  *A61B 90/00*  (2016.01)
  *G06T 7/215*  (2017.01)
  *A61B 17/3211* (2006.01)
  *A61B 1/07*   (2006.01)
  *A61B 34/30*  (2016.01)
  *A61B 17/00*  (2006.01)
  *A61B 90/30*  (2016.01)

(52) U.S. Cl.
  CPC ..... *A61B 34/30* (2016.02); *A61B 2017/00221* (2013.01); *A61B 2017/00699* (2013.01); *A61B 2090/306* (2016.02); *A61B 2090/365* (2016.02); *A61B 2090/3612* (2016.02); *A61B 2090/373* (2016.02); *G06T 2207/10016* (2013.01); *G06T 2207/10068* (2013.01); *G06T 2207/30104* (2013.01)

(56) References Cited

U.S. PATENT DOCUMENTS

| | | |
|---|---|---|
| 2007/0135705 A1 | 6/2007 | Lorenz et al. |
| 2011/0026790 A1 | 2/2011 | Kargar et al. |
| 2013/0322729 A1* | 12/2013 | Mestha ............ A61B 5/02 |
| | | 382/134 |
| 2014/0039303 A1* | 1/2014 | Kanzaki ............ A61B 6/12 |
| | | 600/424 |
| 2014/0313303 A1 | 10/2014 | Davis et al. |
| 2015/0257653 A1 | 9/2015 | Hyde et al. |
| 2016/0113500 A1 | 4/2016 | Gross et al. |

OTHER PUBLICATIONS

"Video Magnification," CSAIL, https://people.csail.mit.edu/mrub/vidmag, 1 page, Dec. 27, 2016.

Amir-Khalili et al., "Automatic segmentation of occluded vasculature via pulsatile motion analysis in endoscopic robot-assisted partial nephrectomy video," Medical Image Analysis 25 (2015), pp. 103-110.

Adams et al., "Algorithm-Based Motion Magnification for Video Processing in Urological Laparoscopy," Journal of Endourology, vol. 31, No. 6, Jun. 2017, pp. 583-587.

Liu et al., "Motion analysis and removal in intensity variation based OCT angiography," Biomedical Optics Express, vol. 5, No. 11, Nov. 2014, 16 pages.

Porter et al., "Compositing Digital Images," Computer Graphics, vol. 18, No. 3, Jul. 1984, pp. 253-259.

International Search Report and Written Opinion from the International Searching Authority dated May 30, 2018, for International Application No. PCT/US2018/023173, filed Mar. 19, 2018, 15 pages.

* cited by examiner

DETECTION OF BLOOD VESSELS

RELATED APPLICATIONS

This application claims the benefit of U.S. Provisional Application No. 62/474,774, filed Mar. 22, 2017, which is incorporated by reference in its entirety.

TECHNICAL FIELD

This disclosure relates generally to surgical systems, and in particular but not exclusively, relates to computer-assisted surgery.

BACKGROUND INFORMATION

In recent years, computer-assisted surgery has become a popular way to overcome limitations of existing surgical procedures, and possibly enhance the capabilities of doctors performing the surgery. For example, without computerized equipment, doctors may be limited to where they can operate/examine due to the size of their hands and limited dexterity with tools. This inhibits the ability of doctors to operate on small or deep internal tissues.

In open surgery, computer-guided instruments can replace traditional (hand-held) tools to perform operations like rib spreading due to the computer-guided instruments' smoother feedback assisted motions. Robotic systems like these have been shown to reduce or eliminate tissue trauma commonly associated with invasive surgery. Moreover, these instruments may prevent doctors from making accidental mistakes while operating.

However, not all advancements in surgery are necessarily mechanical; diagnostic methods can be used to inform surgeons as they work. For example, specific tissue types may be flagged with fluorescent dyes or the like. However, often these dyes are nonspecific (illuminating a variety of tissues) and may be somewhat toxic to the body. Accordingly, room for advancement exists in the field of computer-guided surgery.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus and method for the detection of blood vessels are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Even when superficial, blood vessels (arteries, capillaries, and veins) are not always clearly visible during a surgical procedure. If the surgeon operates close to blood vessels, there is a risk of accidental bleeding. Such damage might jeopardize the procedure and the consequences may be dire. The surgeon can use coagulation or clipping if he/she notices the damage right-away, but both of these options are time-consuming, and coagulation (e.g., using a monopolar or bipolar device) induces charring. This disclosure aims to highlight blood vessels on a video stream (that the surgeon sees) from an endoscope, surgical robot, or other assistive surgical device, thus reducing the risk of accidental damage to blood vessels.

Generally speaking, the system here takes as inputs (1) the video stream from the endoscope, and (2) the heart rate of the patient undergoing the procedure (e.g., from a heart rate monitor), and outputs the same video stream but with blood vessels highlighted. In many embodiments, blood vessels are made visible because their motion—which otherwise could not be perceived—is amplified, and other motions whose frequencies are not at the heart rate (camera shake, patient moving, etc.) are not amplified. The amplified blood vessel motion may then be used to form a mask of the blood vessels, and the mask is overlaid on the video stream that the physician is using to perform the operation. Such an augmented video is intended to be presented to the surgeon during the procedure instead of the raw video, thus reducing the risk of accidental damage to blood vessels.

One advantage of overlaying a blood vessels mask on the source video is that in case of a true positive alert (i.e., the method correctly highlights the vessel) the surgeon will not ignore the vein/artery. In case of a false negative (i.e., the vessel wasn't highlighted), the surgeon still sees the usual surgical field and can assess the situation as he/she would have done in the absence of augmented reality—that is to say the method described in this disclosure has not removed or hidden any information that is visually available to the surgeon. In the case of a false positive (i.e., a non-existent vessel was highlighted) the surgeon can interpret the mask as being unlikely and ignore it and/or disable the overlay. Thus, the system doesn't create new risks, and simultaneously reduces existing surgical risks. In general, the surgeon can view the results in light of his/her own knowledge of the anatomy, and the system is used for guidance.

Figure 1A:
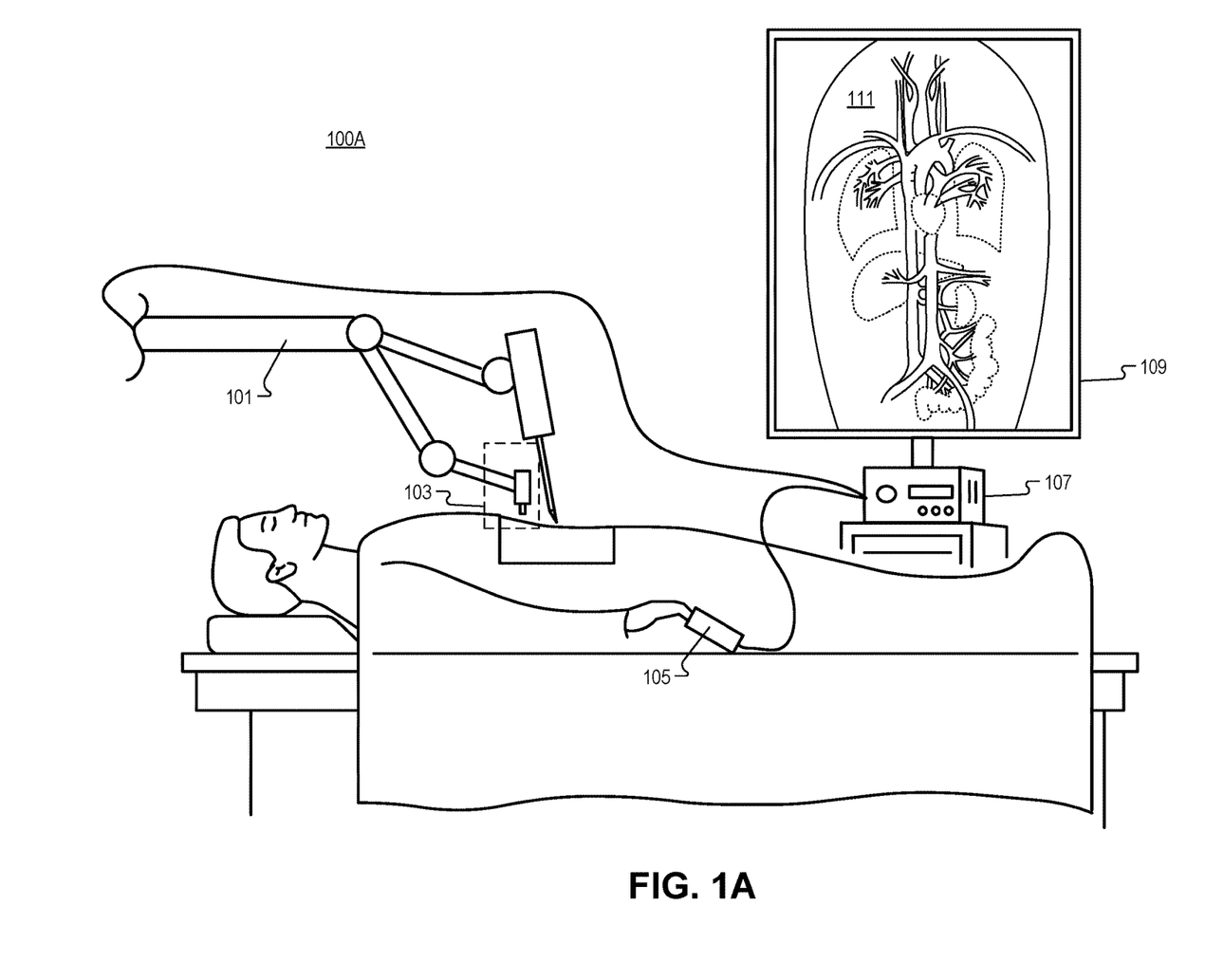
FIG. 1A is an example surgical system for the detection of blood vessels, in accordance with an embodiment of the disclosure.

FIG. 1A is an example surgical system 100A for the detection of blood vessels, in accordance with an embodiment of the disclosure. Surgical system 100A includes surgical robot 101, image sensor 103 (e.g., a video camera), heart rate monitor 105, computer 107 (with a controller which may, in some embodiments, include a processor and memory), and display 109 (displaying an image 111 showing blood vessels highlighted).

As shown, image sensor 103 is coupled to generate video data including a sequence of images of the blood vessels, since it is positioned above the open chest of a patient undergoing surgery. Thus, image sensor 103 captures images in real time of what the surgeon and surgical robot 101 see. However, if advantageous, in some embodiments, image sensor 103 may absorb nonvisible light to collect a nonvisible sequence of images. This may help distinguish the blood vessels if, for example, an IR emitting dye is injected into the patient. Heart rate monitor 105 is coupled to receive the heart rate of the patient and generate heart rate data. In the depicted embodiment, heart rate monitor 105 is coupled to a finger of the patient to measure heart rate optically (e.g., photoplethysmographic signal); however, in other embodiments the heart rate may be monitored in other ways such as using image sensor 103 to functioning as heart rate monitor 105 by looking at the heart beating, or via electrical impulses (measuring the electrical impulses of the heart).

A controller (disposed in computer 107) is coupled to image sensor 103 to receive the video data, and coupled to heart rate monitor 105 to receive the heart rate data. In the depicted embodiment, image sensor 103 and heart rate monitor 105 are directly coupled (wired) to computer 107; but in other embodiments, there may be intervening pieces of circuitry and the signals may be broadcast wirelessly. Similarly, in some embodiments, the controller may be part of a distributed system (e.g., many processors and memory units may be used in the calculations to handle the image processing). In the depicted embodiment, the controller isolates localized motion of the blood vessels in the video data using the heart rate data. In some embodiments, localized motion includes motion with a temporal periodicity that is substantially the same as the heart rate of the patient. The controller may then compute a blood vessel mask, where the blood vessel mask includes differences between the video data (captured by image sensor 103) and the localized motion of the blood vessels. Then the controller may compute combined video data, where the combined video data includes the video data and the blood vessel mask.

As shown, the combined video data may then be sent to display 109, which is coupled to the controller (in computer 107) to receive the combined video data. In response to receiving the combined video data, display 109 may show the sequence of images (video stream) with the blood vessel mask superimposed on the sequence of images. This is depicted as image 111 where the vessels are clearly shown (solid lines) but the organs are less visible (dashed lines). The blood vessel mask may be imposed on the sequence of images and accentuated by using a bright color like green (not commonly found in the human body) or the like. One of ordinary skill in the relevant art will appreciate that there are any number of ways to accentuate the blood vessels, in accordance with the teachings of the present disclosure.

In some embodiments (e.g., where the patient being operated on is not perfectly still), the controller may further include logic that when executed by the controller causes the controller to remove bulk motion (e.g., motion that has a greater magnitude than the localized motion) from the video data. This may be done by comparing sequential images in the sequence of images (constructing a temporal neighborhood), and removing motion between sequential images having a magnitude greater than a threshold magnitude. In order to remove bulk motion from the input video stream (e.g., respiration, camera motion), one can, for example, for each frame of the input video stream: (1) Construct its temporal neighborhood. For all real-time applications, a left-sided neighborhood can be used so that minimal latency is introduced (i.e., only frames prior to the frame of interest are used). Since heart rates are typically 60-100 bpm, a temporal neighborhood of a few seconds should be sufficient. And (2) warp all the frames in the neighborhood of the current frame, borrowing motion estimation methods used in video encoders with large blocks (e.g., >16×16 pixels). This removes bulk motion but keeps motion occurring at a smaller scale. Alternatively or additionally, the processor may convert the video data into low-resolution video data (where the low-resolution video data does not show the localized motion of the blood vessels), and remove motion shown in the low-resolution video data from the video data.

In some embodiments, the controller may also filter the blood vessel mask to remove anomalies in the localized motion of the blood vessels. For example, filtering may be performed by a neural net (e.g., utilizing a radial basis function, self-organizing network, learning vector quantization, or the like), where the neural net has been trained to recognize the blood vessels (e.g., the tree-like structures characteristic of blood vessels).

In the depicted embodiment, only part of surgical robot 101 is shown (there may be other parts disposed off the page). Also, surgical robot 101 has two arms: one with image sensor 103, and one with a scalpel. However, in other embodiments surgical robot 101 may have any number of arms with a variety of instruments (clamps, tweezers, etc.). As shown, the arms may have a number of joints with multiple degrees of freedom so that the system can move freely with as many, or more, degrees of freedom as a surgeon. Additionally, surgical robot 101 may provide haptic feedback to the surgeon by way of pressure/strain/stress sensors disposed in the arms/instruments of the robot 101. Furthermore, a plurality of image sensors 103 may be used to form the sequence of images; the images may be stitched together or the like. Multiple heart rate monitors, or different types of heart rate monitors, may be used to provide redundant data to the system in the event of clearly erroneous heart rate measurements (or for the averaging of multiple measurements to ensure data stability).

Figure 1B:
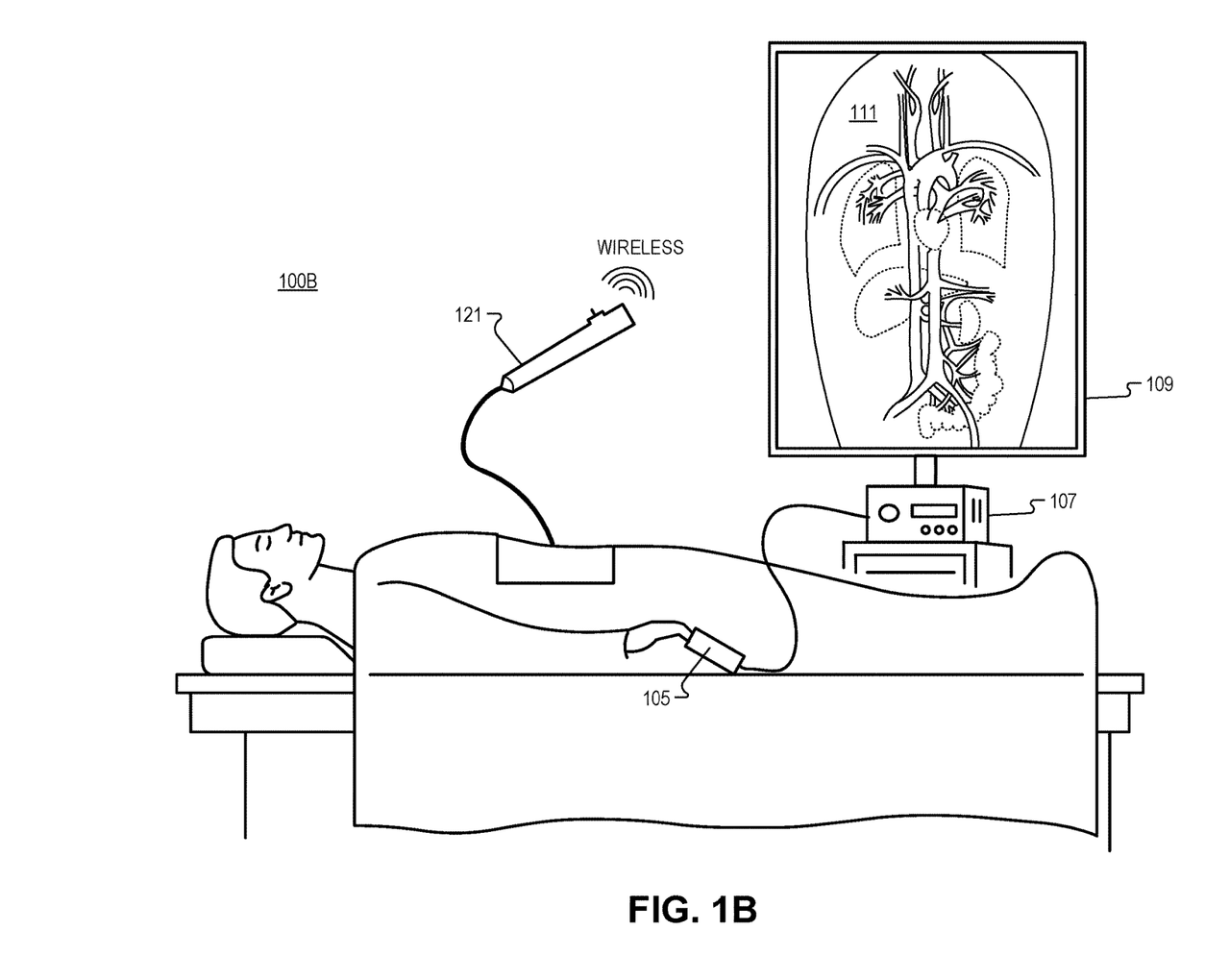
FIG. 1B is an example surgical system for the detection of blood vessels, in accordance with an embodiment of the disclosure.

FIG. 1B is an example surgical system 100B for the detection of blood vessels, in accordance with an embodiment of the disclosure. Surgical system 100B is similar in many respects to surgical system 100A in FIG. 1A; however, one major difference is that an endoscope 121 is used instead of the surgical robot to provide images of the blood vessels of the patient. Moreover, endoscope 121 may wirelessly transfer the images to the controller (in computer 107) to improve the surgeon's mobility/dexterity. Endoscope 121 may be inserted into the patient (as shown) to image small areas and perform minor surgery. System 100B illustrates that the blood vessel detection systems and methods disclosed are compatible with a variety of surgical procedures and instruments, as one of ordinary skill in the art will appreciate.

Figure 2:
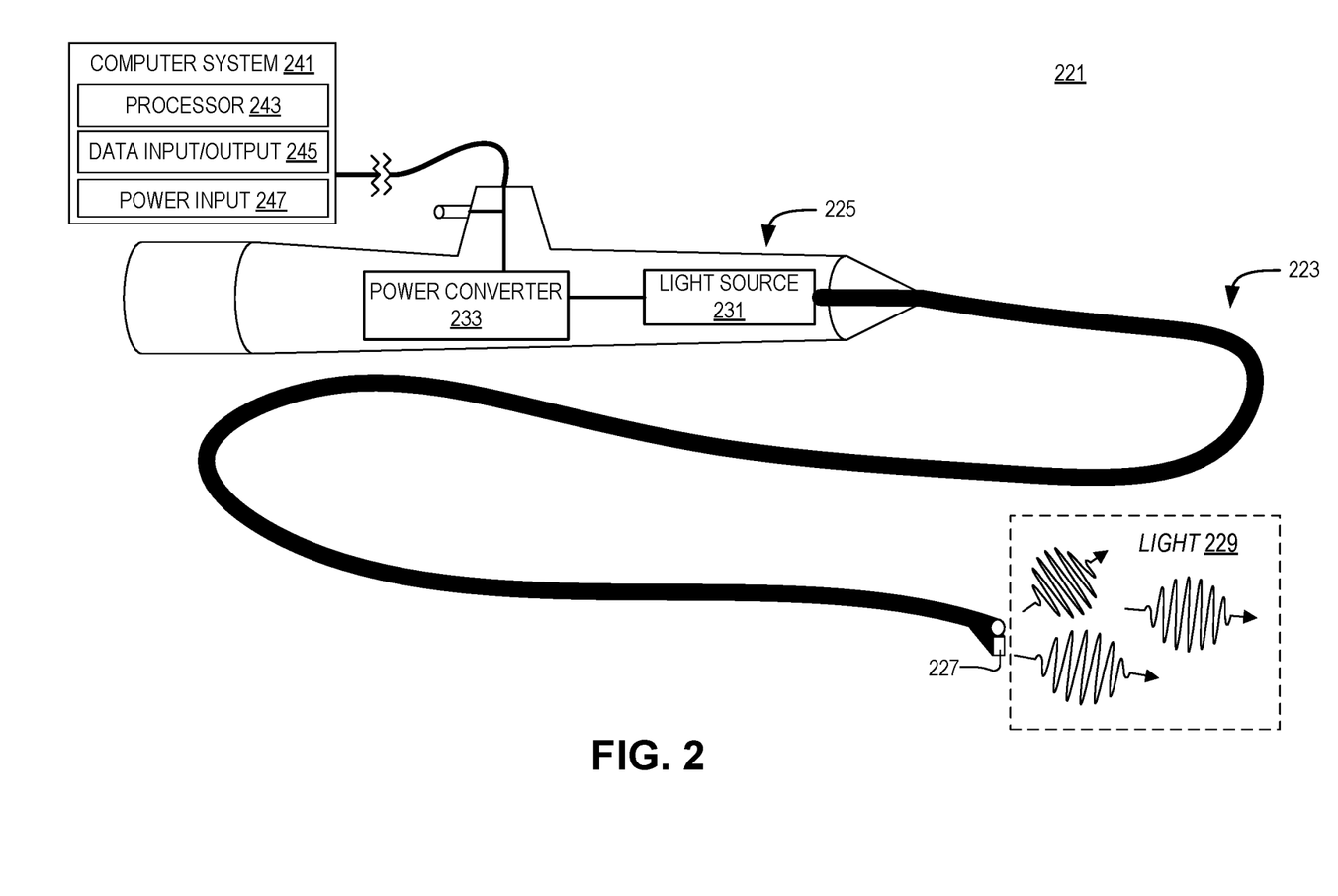
FIG. 2 is an example endoscope which may be used in the surgical system of FIG. 1B, in accordance with an embodiment of the disclosure.

FIG. 2 is an example endoscope 221 which may be used in the surgical system 100B of FIG. 1B, in accordance with an embodiment of the disclosure. Endoscope 221 includes fiber optic cable 223, body 225, image sensor 227, light source 231, and power converter 233.

Endoscope system 221 includes a proximal end (hand held), and a distal end (end of fiber optic cable 223 closest to image sensor 227). Light source 231 is optically coupled to the proximal end of the fiber optic cable 223 to emit visible light 229 into fiber optic cable 223 for output from the distal end. Image sensor 227 is coupled to the distal end of fiber optic cable 223 and positioned to receive a reflection of visible light 229 as reflected visible light. Image sensor 227 then generates a series of images which may form video data. This video data is then sent to computer system 241 which may include a controller with processor 243. Computer system 241 may be internal or external to endoscope 221. Endoscope 221 is also coupled to data input/output 245 (to send image data) and power input 243 to power endoscope 221.

Figure 3:
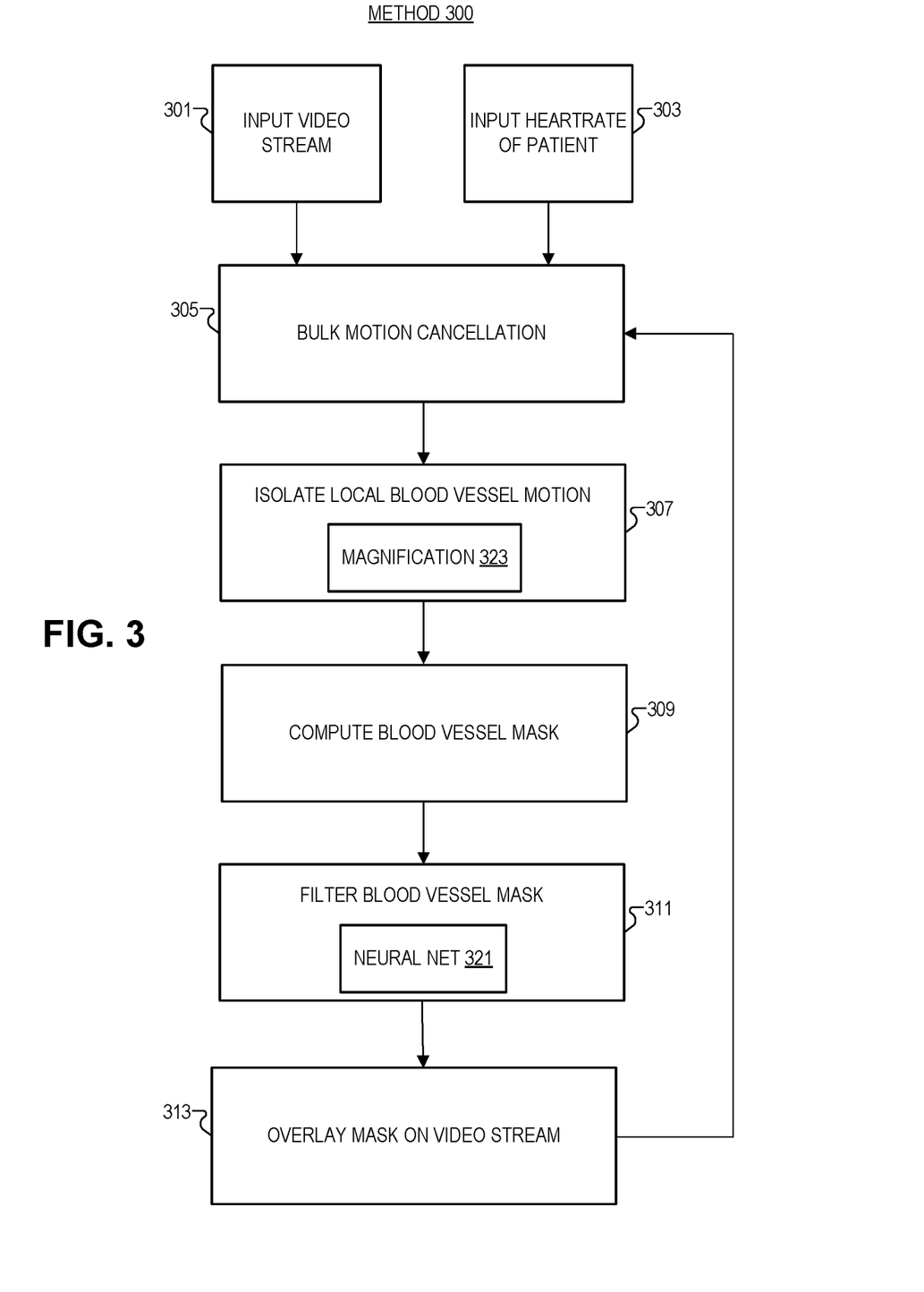
FIG. 3 is a flow-chart describing a method of motion-based detection of blood vessels, in accordance with several embodiments of the disclosure.

FIG. 3 is a flow-chart describing a method of motion-based detection of blood vessels, in accordance with several embodiments of the disclosure. The order in which some or all of process blocks appear in method 300 should not be deemed limiting. Rather, one of ordinary skill in the art having the benefit of the present disclosure will understand that some of method 300 may be executed in a variety of orders not illustrated, or even in parallel. Moreover process blocks may be added or removed in other embodiments of the disclosure. Method 300 may be at least in part cyclical, as illustrated.

Block 301 shows inputting a video stream into a controller/processor. In one embodiment this may include capturing a sequence of images (including the blood vessels) with a video camera, where the video camera generates video data from the sequence of images. The video data is then sent to a processing apparatus.

Block 303 illustrates inputting the heart rate of the patient. In one embodiment this may include recording a heart rate of a patient with a heart rate monitor, where the heart rate monitor generates heart rate data from the heart rate of the patient. The heart rate monitor may send heart rate data to the processor.

Block 305 describes bulk motion cancellation. In many embodiments, bulk motion cancellation is useful since it is likely that the patient or camera may move and thus change the view of the blood vessels. Generally speaking, the bulk motion has a greater magnitude of motion than the localized motion (e.g., if the camera is bumped, the image will move more than if a blood vessel is pulsating). One of ordinary skill in the art can appreciate that bulk motion cancellation can be achieved in a number of ways including but not limited to analyzing the movement between subsets of sequential frames in the video captured, or converting the video data to low-resolution video data (where the low-resolution video data does not show the localized motion of the blood vessels) and removing motion shown in the low-resolution video data from the video data. Other known video stabilization techniques may also be used.

Block 307 shows isolation of local blood vessel motion. After the video data and the heart rate data from the video camera and the heart rate monitor, respectively, are received with a processor, the localized motion of the blood vessels in the video data may be isolated by the processor using the heart rate of the patient. For example, the heart rate may be used to identify portions of the image that are pulsing/moving at substantially the same rate as the heartbeat of the patient. In other words, localized motion includes motion with a temporal periodicity that is substantially the same as the heart rate of the patient.

As shown block 305 includes magnification block 323. In some embodiments local blood vessel motion may be magnified in order to produce an accurate blood vessel map. For instance, prior to isolating localized motion, localized motion may be magnifying with at least one of Lagrangian motion detection or Eulerian motion detection. Thus, blood vessels are made visible because their motion—which otherwise could not be perceived—is amplified. The frequency magnification range may be set to the patient's heart rate +/− the accuracy of the heart rate monitor, +/− the expected variability of the patient's heart rate, or some other margin. This avoids the magnification of motions which were not caused by the beating of the heart.

Block 309 illustrates computing the blood vessel mask. In some embodiments the blood vessel mask may be the difference between the video data and the localized motion of the blood vessels. Thus to calculate the blood vessel mask the processor may take the portion of the video data pulsing substantially in rhythm with the heart rate of the patient, and subtract the other portions of the image to create a mask just showing the portions of the image pulsating. In one embodiment pulsing may occur at ~60-80 bpm (approximate heart rate of a person) however this may change depending on drugs administered, the fitness of the patient, or the like.

Block 311 describes filtering the blood vessel mask. Because there may be parts of the image (other than the blood vessels) that move with a periodicity close to the heart rate of the patient, or even image artifacts from the image sensor, the blood vessel mask is filtered. In some embodiments this may be achieved by a neural net 321, so that the neural net 321 removes portions of the image that do not resemble the tree-like structures of blood vessels. Similarly, a high pass or low pass filter may be used to remove portions of the image that are not pulsating/moving at the appropriate speeds; this filtering may occur in both the spatial (e.g., a structure too large to be a blood vessel) and temporal (e.g., a structure pulsing too slowly to be a blood vessel) domains. However, one of ordinary skill in the art will appreciate that other filtering techniques may be used to filter the blood vessel mask, in accordance with the teachings of the present disclosure. Moreover, various filtering techniques can be used simultaneously to improve processing efficiency or the like. For example a high pass and low pass filter may be used prior to applying the neural net 321, so clearly erroneous artifacts are removed using very little computing power. Further, the neural net 321 may be trained with images of blood vessels from other surgeries to accommodate the neural net 321 to seeing only a partial view of blood vessels. Further, a human may be used to correct the neural net 321 as it is trained to recognize blood vessels.

Block 313 shows overlaying the blood vessel mask on the video stream. In one embodiment, this may involve computing combined video data (where the combined video data includes the video data and the blood vessel mask) and outputting the combined video data to a display via USB, HDMI, or the like. In one embodiment, combined video data is computed using alpha-blending. In response to the display receiving the combined video data, the display shows the sequence of images with the blood vessel mask superimposed on the sequence of images. In some embodiments, if the overlay is distracting/cumbersome for part of the surgical procedure, the surgeon may select an option to remove the overlay from the image display. In response to this input from the surgeon, the blood vessel mask may be removed from the sequence of images (video) shown on the display. In some embodiments, the system may be voice responsive so that the surgeon can call out commands and the system will respond. For example, the surgeon may call out "OK surgical system, shut off blood vessel overlay" and the system will shut off the overlay. This may allow the surgeon to change display preferences without using his/her hands.

In some embodiments, to ensure real-time, a "past" mask can be applied to the current frame (after being computed on a "past" neighborhood) using traditional optical flow or other motion estimation methods to account for the short-term motion. This is because real time image capture often occurs at 60 fps, but the heart rate is only around 70 bpm.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A system for the detection of blood vessels, comprising:
   an image sensor coupled to generate video data including a sequence of images of the blood vessels;
   a heart rate monitor to measure a heart rate of a patient and to generate heart rate data based on the heart rate; and
   a controller coupled to the image sensor to receive the video data, and coupled to the heart rate monitor to receive the heart rate data, wherein the controller includes logic that when executed by the controller causes the controller to perform operations including:
      isolating localized motion of the blood vessels in the video data using the heart rate data;
      computing a blood vessel mask that includes differences between the video data and the localized motion of the blood vessels;
      filtering the blood vessel mask to remove anomalies in the localized motion of the blood vessels; and
      computing combined video data that includes the video data and the blood vessel mask.

2. The system of claim 1, further comprising a display coupled to the controller to receive the combined video data, and in response to receiving the combined video data, displaying the sequence of images with the blood vessel mask superimposed on the sequence of images.

3. The system of claim 1, wherein the image sensor is included in at least one of a system for robotic surgery or an endoscope system.

4. The system of claim 1, wherein the controller further includes logic that when executed by the controller causes the controller to perform operations including:
   removing bulk motion from the video data.

5. The system of claim 4, wherein removing bulk motion from the video data includes at least one of:
   comparing sequential images in the sequence of images and removing motion between sequential images having a magnitude greater than a threshold magnitude; or
   converting the video data into low-resolution video data, wherein the low-resolution video data does not show the localized motion of the blood vessels, and removing motion shown in the low-resolution video data from the video data.

6. The system of claim 1, wherein filtering is performed by a neural net, and wherein the neural net has been trained to recognize the blood vessels.

7. The system of claim 1, wherein the localized motion includes motion with a temporal periodicity that is substantially the same as the heart rate of the patient.

8. The system of claim 7, wherein the controller further includes logic that when executed by the controller causes the controller to perform operations including:
   magnifying the localized motion with at least one of Lagrangian motion detection or Eulerian motion detection prior to isolating the localized motion of the blood vessels.

9. The system of claim 1, wherein the image sensor absorbs nonvisible light to collect the sequence of images including blood vessels.

10. A method of motion-based detection of blood vessels, comprising:
    capturing a sequence of images including the blood vessels with a video camera, wherein the video camera generates video data from the sequence of images;
    recording a heart rate of a patient with a heart rate monitor, wherein the heart rate monitor generates heart rate data from the heart rate of the patient;
    receiving the video data and the heart rate data from the video camera and the heart rate monitor, respectively, with a processor;
    isolating localized motion of the blood vessels in the video data with the processor using the heart rate of the patient;
    computing a blood vessel mask with the processor, wherein the blood vessel mask includes differences between the video data and the localized motion of the blood vessels;
    filtering the blood vessel mask to remove anomalies in the localized motion of the blood vessels; and
    computing combined video data, wherein the combined video data includes the video data and the blood vessel mask.

11. The method of claim 10, further comprising outputting the combined video data to a display, wherein in response to the display receiving the combined video data, the display shows the sequence of images with the blood vessel mask superimposed on the sequence of images.

12. The method of claim 11, further comprising, in response to input from a user, removing the blood vessel mask from the sequence of images shown on the display.

13. The method of claim 10, wherein capturing the sequence of images includes using an image sensor disposed in at least one of an endoscope or a surgical robot.

14. The method of claim 10, further comprising removing bulk motion from the video data.

15. The method of claim 14, wherein removing bulk motion includes at least one of:
- comparing sequential images in the sequence of images and removing motion with a magnitude greater than a threshold magnitude; or
- converting the video data to low-resolution video data, wherein the low-resolution video data does not show the localized motion of the blood vessels, and removing motion shown in the low-resolution video data from the video data.

16. The method of claim 10, wherein filtering is performed by at least one of a high-pass filter, a low-pass filter, or a neural net, wherein the neural net has been trained to recognize tree-like structures characteristic of the blood vessels.

17. The method of claim 10, wherein the combined video data is computed using alpha-blending.

18. The method of claim 10, wherein the localized motion includes motion with a temporal periodicity that is substantially the same as the heart rate of the patient.

19. At least one non-transitory machine-readable storage medium that provides instructions that, when executed by a machine, will cause the machine to perform operations comprising:
- receiving video data including a sequence of images of blood vessels of a patient;
- receiving heart rate data of the patient;
- isolating localized motion of the blood vessels in the video data using the heart rate data;
- computing a blood vessel mask, wherein the blood vessel mask includes differences between the video data and the localized motion of the blood vessels;
- filtering the blood vessel mask to remove anomalies in the localized motion of the blood vessels; and
- computing combined video data, wherein the combined video data includes the video data and the blood vessel mask.

20. At least one non-transitory machine-readable storage medium that provides instructions that, when executed by a machine, will cause the machine to perform operations comprising:
- receiving video data including a sequence of images of blood vessels of a patient;
- receiving heart rate data of the patient;
- magnifying localized motion of the blood vessels in the video data with at least one of Lagrangian motion detection or Eulerian motion detection prior to isolating the localized motion;
- isolating the localized motion of the blood vessels in the video data using the heart rate data;
- computing a blood vessel mask, wherein the blood vessel mask includes differences between the video data and the localized motion of the blood vessels; and
- computing combined video data, wherein the combined video data includes the video data and the blood vessel mask.

21. At least one non-transitory machine-readable storage medium that provides instructions that, when executed by a machine, will cause the machine to perform operations comprising:
- receiving video data including a sequence of images of blood vessels of a patient;
- receiving heart rate data of the patient;
- removing bulk motion from the video data by:
  - converting the video data into low-resolution video data, wherein the low-resolution video data does not show localized motion of the blood vessels; and
  - removing the bulk motion shown in the low-resolution video data from the video data;
- isolating the localized motion of the blood vessels in the video data using the heart rate data after removing the bulk motion from the video data;
- computing a blood vessel mask, wherein the blood vessel mask includes differences between the video data and the localized motion of the blood vessels; and
- computing combined video data, wherein the combined video data includes the video data and the blood vessel mask.

* * * * *